(12) United States Patent
Kern

(10) Patent No.: US 6,486,348 B1
(45) Date of Patent: Nov. 26, 2002

(54) METHOD FOR PRODUCING 1-METHYL-3-NITROGUANIDINE

(75) Inventor: Norbert Kern, Haltern am See (DE)

(73) Assignee: Nigu Chemie GmbH, Waldkraiburg (DE)

(*) Notice: Subject to any disclaimer, the term of this patent is extended or adjusted under 35 U.S.C. 154(b) by 0 days.

(21) Appl. No.: 10/161,619

(22) Filed: Jun. 5, 2002

Related U.S. Application Data

(63) Continuation of application No. PCT/EP01/00351, filed on Jan. 12, 2001.

(30) Foreign Application Priority Data

Jan. 28, 2000 (DE) .......................... 100 03 834

(51) Int. Cl.$^7$ .................. C07C 277/08; C07C 279/04; C07C 279/36
(52) U.S. Cl. ........................................ 564/108
(58) Field of Search .......................... 564/108

(56) References Cited

U.S. PATENT DOCUMENTS

| 5,245,040 A | * | 9/1993 | Maienfisch et al. ......... 546/332 |
| 5,783,734 A | | 7/1998 | Gallenkamp et al. |
| 6,384,277 B1 | | 5/2002 | Pabst et al. |

FOREIGN PATENT DOCUMENTS

| DE | 199 56 593 | 5/2000 |
| EP | 0 798 293 | 10/1997 |
| WO | WO 01/51458 | 7/2001 |

OTHER PUBLICATIONS

Hardy–Klein, Muriel L., "The Denitration of –Methyl–N'–nitroguanidine". J. Chem. Soc., 70–80 (1957).

Davis, Tenney L., et al., "Studies in the Urea Series. Transformations of Nitroguanidine". Proc. Am. Acad. Arts Sci., 61, 437–457 (1926).

McKay, A. F., et al., "Preparation and properties of –Methyl—nitroso–N'–nitroguanidine". JACS, 69, 3028–3030 (1947).

* cited by examiner

*Primary Examiner*—Brian J. Davis
(74) *Attorney, Agent, or Firm*—Nath & Associates PLLC; Gary M. Nath; Todd L. Juneau

(57) ABSTRACT

The invention relates to a method for producing 1-methyl-3-nitroguanidine. According to said method, nitroguanidine is reacted with methylamine and/or a methylammonium salt in an aqueous solution, at temperatures of 30 to 60° C. and at a pH value of 95 to 12.3. In this way, yields of 1-methyl-3-nitroguanidine of at least 80% and degrees of purity>99% can be obtained in a particularly environmentally friendly and technically simple way.

15 Claims, No Drawings

METHOD FOR PRODUCING 1-METHYL-3-NITROGUANIDINE

This application is a Continuation of International Application No. PCT/EP01/00351 with an international filing date of Jan. 12, 2001, the entire contents of which are hereby incorporated by reference in their entirety.

TECHNICAL FIELD

The present invention relates to a method for producing 1-methyl-3-nitroguanidine which is an important intermediate product for the production of biologically active compounds, in particular insecticides (cf. "Nicotinoid Insecticides and the Nicotinic Acetylcholine Receptor", I. Yamamoto, J. E. Casida (ed.), Springer Verlag, Tokyo, 1999).

PRIOR ART

A series of proposals has already been made in the prior art regarding the production of 1-methyl-3-nitroguanidine. One known method of production is the dehydration of methyl guanidine nitrate with the help of sulfuric acid (cf. J. Amer. Chem. Soc., 1933, pp. 55, 731). The corresponding methyl guanidine nitrate is, according to U.S. Pat. No. 2,425,341, available from an aqueous cyanamide solution and methylammonium nitrate, however the method is unsatisfactory due to the relative minor yield and the necessary post-purification.

According to the method variant described in WO 98/43 951 methyl guanidine nitrate is obtained by reacting methylammonium nitrate with water-free cyanamide in organic solvents, such as ether or alcohols, and thereafter is reacted directly into 1-methyl-3-nitroguanidine. The use of water-free cyanamide is not, however, economical as compared to aqueous cyanamide solutions.

It is furthermore known that 1-methyl-3-nitroguanidine can be obtained by nitration of methyl guanidine sulfates (cf. J. Amer. Chem. Soc., 1933, pp. 55, 731). This method of production also has the disadvantage of a unsatisfactory yield as well as a relative large amount of waste water.

The reaction of methylammonium nitrate with calcium cyanamide or dicyandiamide (cf. Can. J. Chem., 1958, 36, 737) also leads to unsatisfactory results since the purity of the methyl guanidine nitrate obtained by this means is less than 90%.

A further method for the production of 1-methyl-3-nitroguanidine is that methylisothiourea sulfate is first nitrated and thereafter the methylmercapto group is substituted by a methyl amino residue (cf. J. Amer. Chem. Soc., 1954, 76, 1877). The splitting of methyl mercaptan, especially when performing the method on a large industrial scale, causes considerable operational problems.

Moreover it is known that 1-methyl-3-nitroguanidine can be obtained in that a greatly alkaline nitroguanidine solution is reacted at 60° C. with a large excess of methylammonium chloride (cf. J. Amer. Chem. Soc., 1947, 69, 3028 and J. Chem. Soc. 1957, 70). With this process, the purity of the final products which must be purified in complicated methods, and in particular the individual yields attained of pure product of between 43 and 66% are very unsatisfactory. Very large amounts of urea or guanidine derivates results as by-products with a development of gaseous $N_2O$. Moreover large amounts of waste water also result.

The direct reaction of aqueous methyl amine solutions with nitroguanidine at temperatures of >60° C. (cf J. Amer. Chem. Soc., 1927, pp. 49, 2304, and Proc. Am. Acad. Arts Sci., 1926, pp. 61, 437) results with only insufficient yields of 36 to 45% in 1-methyl-3-nitroguanidine.

The same disadvantages are also shown by the direct reaction described in EP-A 798 293 of a methylamine solution with nitroguanidine at 0–40° C. The desired final product is obtained also with this manner of procedure with only a maximum yield of 60%. The method is moreover very uneconomical due to the long reaction times of about 24 hours and the high dilution which leads, with the insufficient yields of space/time, to very large amounts of waste water.

Representation of the Invention

The present invention was therefore based on the object to develop a method for the production of 1-methyl-3-nitroguanidine which does not have the disadvantage of the prior art, but that allows the desired final product to be acquired with at good yields and high purity in an especially environmentally sound manner and by a technically simple means.

This object was solved according to the invention in that nitroguanidine was reacted with methylamine and/or a methylammonium salt in an aqueous solution at temperatures of 30 to 60° C. and at a pH value of 9.5 to 12.3. It was surprisingly found that the formation of $N_2O$ was also considerably reduced along with an increase in yields, by means of which the danger of formation of explosive mixtures with the ammoniac formed as a by-product is considerably reduced.

Thus nitroguanidine with methylamine and/or a methyl ammonium salt is reacted in methods according to the invention in an aqueous solution at temperatures of 30 to 60° C., in particular 40 to 45° C.

The salts of strong mineral acids, such as e.g. the sulfate, hydrochloride, nitrate or phosphate, are used as methylammonium salts.

It is to be considered essential to the invention that the pH value is adjusted during the reaction to a value of 9.5 to 12.3. Surprisingly, it was found that the yields obtainable depend to a great extent on the pH value during the reaction. When the method according to the prior art was reproduced, it was found that pH values of 13.0 to 14.0 occur thereby which always lie above the $pK_a$ value of nitroguanidine (12.4). With such reaction conditions, yields of clearly above 60% cannot be obtained due to the side reactions. If the reaction is performed on the other hand at a pH value below the $pK_a$ value of nitroguanidine, yields amounting to 80 to 95% are obtained. pH values of 11.0 to 12.0 during the reaction have proven to be especially advantageous here. The yields are again reduced if the pH values lie clearly below 9.5.

The adjustment of the pH value takes place either by the addition of the methyl amine and the methylammonium salt in such a molar ratio that the desired pH value adjusts itself, or by the usual use of strong bases or acids. A mineral acid, selected from the group sulfuric acid, hydrochloric acid, nitric acid or phosphoric acid, is used preferably as the strong acids, while, for example, sodium hydroxide solution or potassium hydroxide solution are used as strong bases. According to a preferred embodiment, the methylamine and/or the methylammonium salt are used in such an amount that the molar amount of the sum of the two components, based on the nitroguanidine used, corresponds to an excess of 5 to 50 mol-%.

Principally, a higher excess of methylamine and/or methylammonium salt with up to 100% can be used without a substantial formation of the dialkylated product 1,2-dimethyl-3-nitroguanidine being observed thereby. A higher increase than the preferred 5 to 50% by weight of methylamine and/or methylammonium salt, however, decreases the economicability of the method according to the invention.

After the reaction is concluded, which is ended as a rule after 2 to 3 hours, the final product is separated, preferably by filtration. A neutralization of the reaction mixture before the filtration is also possible without this acting negatively in any form on the yield. Optionally, the final product can be subsequently rinsed with some cold water and dried.

The advantages of the method according to the invention consist essentially in that 1-methyl-3-nitroguanidine can be obtained with yields of at least 80% und purities>99% in a manner especially friendly to the environment and technically simple, which is why this method is suited especially for large industrial use.

The following examples should better illustrate the invention.

EXAMPLE 1

100 g (0.63 mol) methylammonium sulfate is dissolved in 400 ml $H_2O$. A pH value of 11.5 is adjusted with about 53 g (0.66 mol) 50% sodium hydroxide solution. In this solution 100 g (0.96 mol) nitroguanidine is stirred at 40 to 42° C. After 3 hours of stirring at 40 to 42° C., the reaction mixture is neutralized at max. 30° C. After being cooled to 5° C. the suspension is filtered off, is washed with 120 ml cold $H_2O$ and dried. 108 g methyl nitroguanidine is obtained (content>99% per HPLC, m.p.: 158–159° C.), corresponding to a yield of 95%.

EXAMPLE 2

While being strongly stirred, 19.8 kg (152 mol) nitroguanidine having a water content of 20% by wt. is added at 40–42° C. to a mixture of 2.65 kg (16.5 mol) methyl ammonium sulfate and 15.4 kg (165 mol) 40%-methylamine solution in 41 l $H_2O$, with the reaction mixture having a pH value of 11.3. After 2 hours the reaction mixture is cooled to 3° C., filtered off, washed and dried 3 times with 6 l cooled $H_2O$ each time. 14.8 kg methyl nitroguanidine (content>99% per HPLC, m.p.: 159° C.) is obtained, corresponding to a yield of 82%.

What is claimed is:

1. A method for producing 1-methyl-3-nitroguanidine, characterized in that nitroguanidine is reacted with methylamine and/or a methylammonium salt in an aqueous solution at temperatures of 30 to 60° C. and at a pH value of 9.5 to 12.3.

2. A method according to claim 1, characterized in that the reaction is performed at a pH value of 11.0 to 12.0.

3. A method according to claim 1, characterized in the respective sulfate, hydrochloride, nitrate or phosphate is used as the methyl ammonium salt.

4. A method according to claim 1, characterized in that the pH value adjustment is undertaken with the help of a strong acid or base.

5. A method according to claim 4, characterized in that a mineral acid, selected from the group consisting of sulfuric acid, hydrochloric acid, nitric acid and phosphoric acid is used as mineral acid.

6. A method according to claim 4, characterized in that a sodium hydroxide solution or a potassium hydroxide solution is used as a strong base.

7. A method according to claim 1, characterized in that the methylamine or the methylammonium salt is used in an amount that the molar amount of the sum of the two components, based on nitroguanidine, corresponds to an excess of 5 to 50 mol-%.

8. A method according to claim 1, characterized in that the reaction is carried out at a temperature of 40 to 45° C.

9. A method according to claim 4, characterized in that the methyl amine or the methylammonium salt is used in an amount that the molar amount of the sum of the two components, based on nitroguanidine, corresponds to an excess of 5 to 50 mol-%.

10. A method for producing 1-methyl-3-nitroguanidine, characterized in that nitroguanidine is reacted with a methylammonium salt in an aqueous solution at temperatures of 30 to 60° C. and at a pH value of 9.5 to 12.3, the pH value adjustment being undertaken with the help of methylamine and/or a strong base.

11. A method according to claim 10, characterized in that the reaction is performed at a pH value of 11.0 to 12.0.

12. A method according to claim 10, characterized in that the respective sulfate, hydrochloride, nitrate or phosphate is used as the methyl ammonium salt.

13. A method according to claim 10, characterized in that a sodium hydroxide solution or a potassium hydroxide solution is used as a strong base.

14. A method according to claim 10, characterized in that the methylamine or the methylammonium salt is used in an amount that the molar amount of the sum of the two components, based on nitroguanidine, corresponds to an excess of 5 to 50 mol-%.

15. A method according to claim 10, characterized in that the reaction is carried out at a temperature of 40 to 45° C.

* * * * *